Sept. 16, 1975 J. C. MIKKELSEN Plant Pat. 3,783
BEGONIA PLANT
Filed Feb. 28, 1974
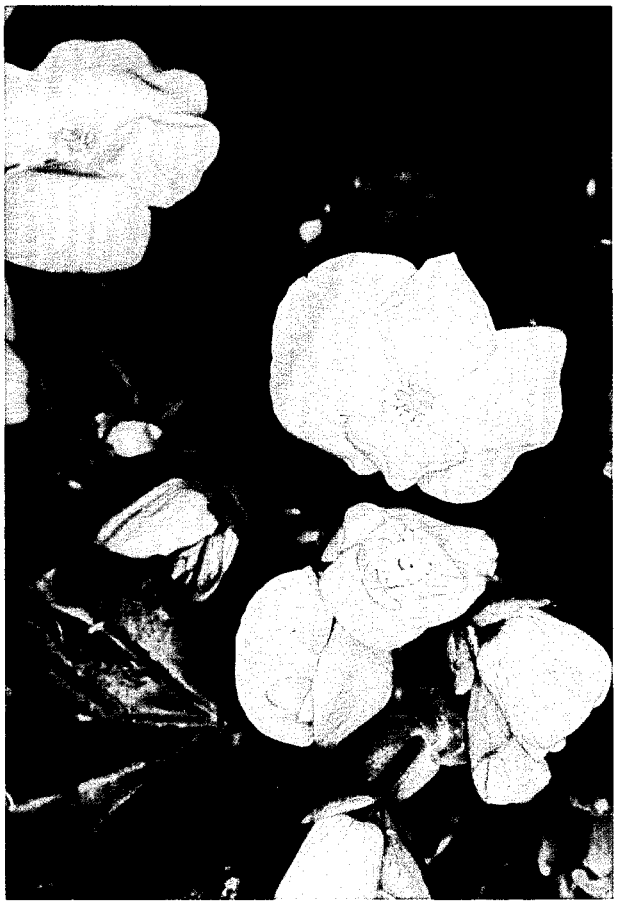

United States Patent Office

Plant Pat. 3,783
Patented Sept. 16, 1975

3,783

BEGONIA PLANT

James C. Mikkelsen, Ashtabula, Ohio, assignor to Mikkelsens Inc., Ashtabula, Ohio

Filed Feb. 28, 1974, Ser. No. 446,787
Int. Cl. A01h *5/00*
U.S. Cl. Plt.—68 1 Claim

The present invention relates to a new and distinctive cultivar of begonia plant, known by the varietal name Schwabenland Salmon and botanically known as *Begonia elatior*. The new variety was discovered by me in a greenhouse in Ashtabula, Ohio, as a mutation in the form of a flowering shoot on a stock plant of the cultivar Schwabenland Pink, an unpatented commercial variety. Asexual reproduction of the new variety by stem and leaf cuttings has reproduced the unique features of the new variety through successive propagations.

The following characteristics distinguish the new begonia from both its parent and other begonias commercially known and used in the floriculture industry:

1. By its distinct salmon pink color, its pastel shade increasing the color range of this class of begonias.
2. The two inside tepals have a slight ruffle and a noticable incurving at the exterior tips.
3. By its rooting more rapidly than the parent variety from which it mutated.
4. The overall growth is less vigorous than its parent.
5. The ability to propagate from leaf cuttings is nearly the same as the parent but with a greater consistency to produce adventitious shoots.
6. Foliage is lush and durable.

The accompanying colored photographic drawing illustrates the overall appearance of this variety taken as a face view of the plant and showing the colors as true as it is reasonably possible to obtain in a colored reproduction of this type.

The following is a detailed description of my new begonia variety based on plants produced under commercial practices in the greenhouses of Mikkelsens, Inc., Ashtabula, Ohio. Color references are made to the Royal Horticultural Society Color Chart except where general color terms of ordinary dictionary significance are used.

*Parentage:* Bud mutation of the cultivar Schwabenland Pink.

*Propagation:* Propagates consistently true to type by leaf cuttings that root in three weeks, thereafter producing adventitious buds that develop into vegetative shoots for controlled flowering. Approximate crop time is 9–10 weeks in high light periods and 14 weeks in low light periods.

*Rooting Habit:* Rapid at 21° C., being fibrous and fine.

*Form:* Upright bushy plant.

*Habit of Growth:* Upright and self-supporting under normal greenhouse practices for begonia culture, with the plant when fully grown being approximately 10″–12″ high and 10″–12″ in diameter.

*Blooming Habits:* Can be manipulated to flower anytime and continue for many months.

*Blooming Season:* Normal (natural) blooming season is early to mid-November. Controlled flowering with light and temperature manipulations allow for year around production. Flower color is best in spring and fall.

*Foliage:* Average quantity for this type of begonia.

- *Size*—Is typical for this class of begonias measuring 8–10 cm. across the blade.
- *Shape*—Cordate, crenate.
- *Texture*—Quite fleshy, firm, glabrous.
- *Margin*—Leaves do not remain flat, wavy between sinus.
- *Color*—Old: top: 147A–B; under: 138B. New: top: 137C; under: 148B.

*Disease Resistance:* Good against common powdery mildew when compared to the so-called Christmas begonia types.

*Flowers:*

- *Borne*—In clusters of individual flowers carried on separate pedicels of the cyme which has a sturdy peduncle giving good placement of blooms throughout the plant. Individual blooms last approximately 2–4 weeks.
- *Quantity*—Average amount for the Schwabenland types.
- *Buds*—Flat—reverse showing the red color 47C.
- *Tepals*—The outer tepals are flat, color between 40D and 33B; two inner tepals have exterior edges curling, color between 32A–30B. Color of tepals of parent cultivar Schwabenland Pink when grown under similar conditions in 43C–D.
- *Reproductive Organs:* Stamens—Abundant—color 13B. Pollen—Color 12D. Styles/ovaries—none observed.

I claim:

1. A new and distinct cultivar of *elatior* begonia characterized particularly by its salmon pink color, the pastel shade increasing the color range of begonias of this class; its two inside tepals which have a slight ruffle and a noticeable incurving of the exterior tips; its rapid rooting; its consistency to propagate from leaf cuttings that root in three weeks, thereafter producing adventitious shoots, and by its lush and durable foliage.

No references cited.

ROBERT E. BAGWILL, Primary Examiner